United States Patent [19]

Harandi et al.

[11] Patent Number: 5,041,690
[45] Date of Patent: Aug. 20, 1991

[54] CONVERSION OF ALCOHOLS TO ETHER-RICH GASOLINE

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 563,731

[22] Filed: Aug. 3, 1990

Related U.S. Application Data

[63] Continuation of Ser. No. 344,585, Apr. 28, 1989, abandoned.

[51] Int. Cl.$^5$ ............................................. C07C 41/06
[52] U.S. Cl. .................................. 568/695; 568/697; 568/698; 568/694; 585/324; 585/314; 585/315; 44/446; 44/449
[58] Field of Search ............... 568/695, 697, 698, 694; 585/324, 314, 315

[56] References Cited

U.S. PATENT DOCUMENTS

| | | | |
|---|---|---|---|
| 4,684,757 | 8/1987 | Avidan et al. | 585/331 |
| 4,777,321 | 10/1988 | Harandi et al. | 585/640 |
| 4,827,046 | 5/1989 | Harandi et al. | 568/697 |
| 4,857,664 | 8/1989 | Huang et al. | |

Primary Examiner—Howard T. Mars
Attorney, Agent, or Firm—Alexander J. McKillop; Charles J. Speciale; L. G. Wise

[57] ABSTRACT

Methanol or other alcohol is converted to high octane gasoline components by an integrated process wherein crude aqueous alcohol feedstock is extracted with a liquid extractant stream containing $C_4+$ iso-olefin and reacted to form tertiary-alkyl ethers, such as MTBE. The aqueous raffinate is converted to olefinic hydrocarbons in a MTO catalytic reactor. Propene from the MTO reaction is reacted with water to produce di-isopropyl ether, which may be blended with MTBE and $C_6+$ MTO hydrocarbons to produce high octane gasoline. Isobutylene and isoamylenes from the MTO reaction can be recovered and recycled as a liquid extractant stream.

11 Claims, 2 Drawing Sheets

CONVERSION OF ALCOHOLS TO ETHER-RICH GASOLINE

This is a continuation of copending application Ser. No. 344,585, filed on Apr. 28, 1989, now abandoned.

BACKGROUND OF THE INVENTION

This invention relates to techniques for converting crude methanol or other $C_1$-$C_4$ lower aliphatic alcohols to alkyl tertiary-alkyl ethers, di-isopropyl ether (DIPE), and gasoline range hydrocarbons. In particular, this invention relates to an integrated system for converting crude methanol to valuable products by etherifying lower branched olefins, such as $C_4$-$C_7$ normally liquid iso-olefins. It is known that isobutylene and other isoalkenes produced by hydrocarbon cracking may be reacted with methanol over an acidic catalyst to provide methyl tertiary butyl ether (MTBE) and isoamylenes may be reacted with methanol over an acidic catalyst to produce tertiary-amyl methyl ether (TAME). Those ethers having the formula $CH_3$—O—R, where R is a tertiary alkyl radical, are particularly useful as octane improvers for liquid fuels, especially gasoline.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel $(R+0=91)$ is about 120. For a fuel with a low motor rating $(M+0=83)$ octane, the blending value of MTBE at the 10% level is about 103. On the other hand, for an $(R+0)$ of 95 octane fuel, the blending value of 10% MTBE is about 114.

Increasing demand for high octane gasolines blended with lower aliphatic alkyl ethers as octane boosters and supplementary fuels has created a significant demand for isoalkylethers, especially the $C_5$ to $C_7$ methyl alkyl ethers, such as methyl tertiary butyl ether (MTBE) and tertiary amyl methyl ether (TAME). Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %; however, the present invention is useful for removing water in lesser amounts or greater.

It is main object of the present invention to provide a novel and economic technique for removing excess water from crude methanol feedstocks, including novel operating methods and equipment for treating these oxygenate feedstocks prior to etherification and disposing of raffinate containing methanol. It has been discovered that aqueous methanol streams, such as etherification feedstock extraction byproduct can be economically upgraded by catalytic conversion concurrently with hydrocarbons.

SUMMARY OF THE INVENTION

A continuous technique has been found for converting crude methanol to high octane gasoline and mixed ethers. A process is provided for converting crude aqueous alcohol feedstock to tertiary-butyl ether and tertiary-amyl methyl product in contact with acid catalyst comprising the steps of: contacting the aqueous alcohol feedstock with liquid hydrocarbon extractant comprising $C_4$-$C_5$ mixed olefinic hydrocarbons comprising isobutylene and isoamylenes under liquid extraction conditions; recovering an aqueous raffinate phase containing alcohol and a major amount of water introduced with the feedstock; recovering an organic extract phase comprising the hydrocarbon extractant and a portion of alcohol introduced in the feedstock sufficient to etherify a major amount of tertiary olefins in the extract phase; and catalytically converting alcohol in the raffinate phase to predominantly lower olefins rich in propene and isoalkene hydrocarbons, reacting extracted alcohol with the isobutylene and isoamylenes under catalytic etherification reaction conditions to produce predominantly $C_5$+ t-alkyl ethers. Isoalkenes produced by catalytic conversion of alcohol can be recovered in a $C_4$-$C_5$ liquid stream containing isobutenes isoamylenes or mixtures thereof, and employed as liquid extractant. By reacting propene recovered from alcohol conversion with water to produce di-isopropyl ether, an additional octane booster ether product is obtained.

A significant process improvement is provided wherein byproduct isopropanol is coproduced with di-isopropyl ether by reaction of propene with water. The isopropanol may be converted to hydrocarbons concurrently with raffinate alcohol, or at least a portion of the byproduct isopropanol, di-isopropyl ether and tertiary-alkyl ether may be blended with liquid $C_6$+ hydrocarbons to produce high octane gasoline product.

It is a particular object of this invention to provide a process useful for converting feedstock containing methanol and about 2 to 20 wt % water. A typical t-alkyl ether catalyst is sulfonic acid resin. In the secondary effluent conversion stage, the methanol is converted to olefinic hydrocarbons advantageously with a medium pore shape selective metallosilicate catalyst, such as ZSM-5 zeolite. These and other objects and features of the invention will be understood from the following description and in the drawing.

DRAWINGS

FIG. 1 of the drawing is a schematic etherification process flowsheet depicting the present invention;

FIG. 2 is a typical fluidized bed reactor system adaptable for conversion of methanol.

DETAILED DESCRIPTION

Typical feedstock materials for etherification reactions crude methanol commercially available from syngas processes, which may contain up to 30 wt % water, which must be removed, preferably to a methanol purity of about 99.8 wt %. It has been found that more than 75% of crude feedstock methanol can be recovered by liquid extraction with light olefinic liquid extractant, such as butenes and $C_5$+ light olefinic naphtha. The typical hydrocarbon feed ratio range is about 2 to 8 parts per part by weight of extracted methanol.

Typical processing equipment operatively connected according to the present invention includes a continuous feedstock separation and etherification reactor system for converting crude methanol oxygenate feedstock and iso-olefin to methyl t-alkyl ether, wherein the unit operation apparatus includes: extractor means for contacting crude feedstock liquid containing a minor amount of water with a liquid hydrocarbon extraction stream under extraction conditions favorable to selective extraction of methanol, thereby providing an extract liquid stream containing sufficient methanol for etherification and an aqueous raffinate stream lean in methanol; first catalytic reactor means operatively connected for contacting the extract stream in a catalytic reaction zone with acid etherification catalyst in an etherification reaction zone under process conditions to convert a major portion of methanol to ether; second catalytic reactor means for contacting said raffinate stream with methanol conversion catalyst in the presence of hydrocarbon to produce olefinic hydrocarbons; means for charging at least a portion of said olefinic hydrocarbon rich in $C_4$-$C_5$ iso-olefin liquid from said second reactor means to said extractor means as said extraction stream; means for separating water and a propylene-rich $C_3$ stream from said second reactor means; and third reactor means for contacting said propylene-rich $C_3$ stream with water under etherification conditions with a solid catalyst to produce di-isopropyl ether.

Figure 1:
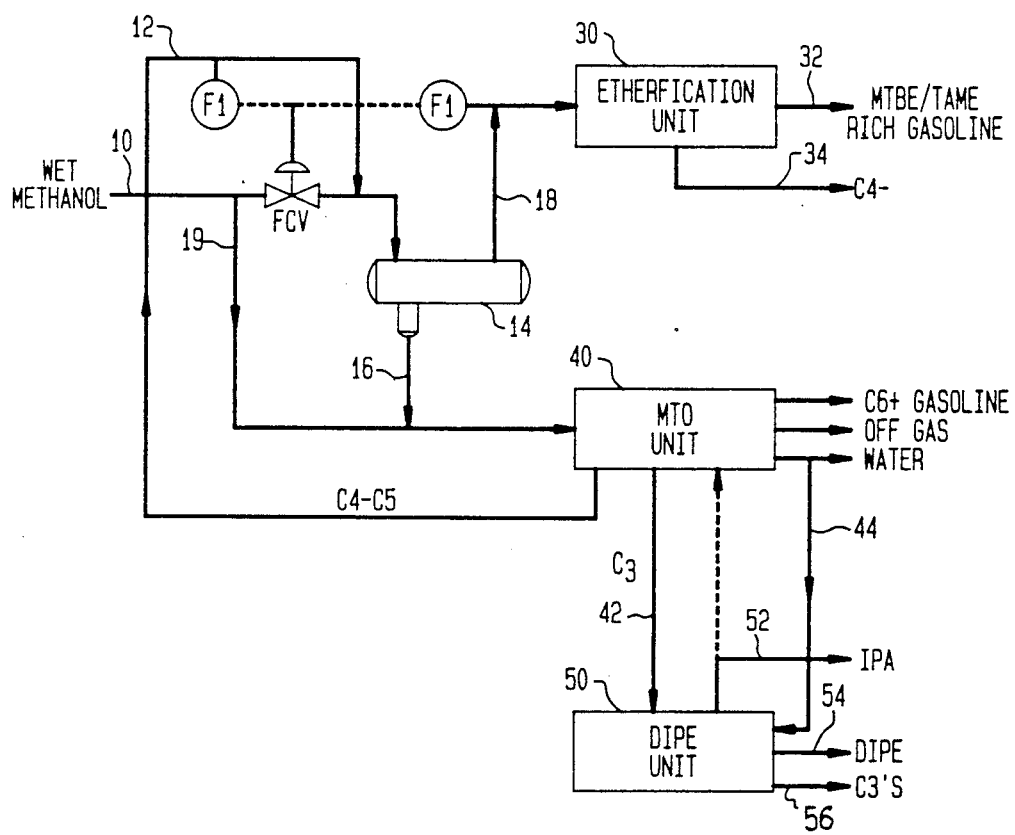

Referring to FIG. 1 of the drawing, a continuous stream of crude methanol (MeOH) feedstock is introduced via conduit 10 with a stream of $C_4+$ olefinic hydrocarbon liquid extractant introduced via conduit 12 to a top inlet of extraction separation unit 14, operated at about 35°-40° C. The fluid handling system includes flow control valve means FCV responsive to flow sensors F1 for conduits 12 and 18. These streams are contacted under liquid extraction conditions to provide an aqueous raffinate phase. An aqueous stream containing a major amount of the water present in the crude feedstock is withdrawn via conduit 16. The lighter organic extract phase containing hydrocarbon extraction solvent and the major amount of feedstock methanol is recovered from extraction unit 14 via conduit 18, and introduced under temperature and process conditions suitable for conversion of methanol in contact with etherification catalyst in a first reactor unit 30. From reactor 30, the effluent product stream passes to a debutanizer or fractionation tower (not shown), where the $C_5+$ methyl tert-alkyl ether product is recovered as a liquid stream 32, along with unreacted $C_5+$ hydrocarbons in the extractant. Tower overhead comprising unreacted $C_4-$ hydrocarbons and methanol are recovered by line 34.

The aqueous raffinate stream 16 consists essentially of water, partitioned methanol (50-80 wt %) and a trace of hydrocarbon. This stream is reactive at elevated temperature in the presence of an acid zeolite catalyst, such as medium pore shape selective zeolite, such as, ZSM-5, etc., in a MTO conversion unit 40, typically a fluidized bed reaction zone. Optionally, the aqueous methanol raffinate stream may be coreacted with unextracted feedstream 19, which bypasses the flow control valve FCV associated with etherification reactant flow. Olefinic light gas and/or other reactive hydrocarbon feedstreams may also be converted in a MTO reaction section, as described by Owen et al in U.S. patent application Ser. No. 006407 filed 23 Jan 1987, now U.S. patent Ser. No. 4,746,762 incorporated herein by reference. The aqueous methanol may be introduced as a liquid directly to the reaction zone (bottom or middle section), as herein described with regard to FIG. 2, or vaporized and mixed with diluent and/or supplemental hydrocarbon feed.

The propene-rich $C_3$ Stream 42 and stream 44 containing a portion of byproduct water from the MTO unit 40 are contacted with an acid etherification catalyst in DIPE unit 50 to produce di-isopropyl ether, which may be recovered by conventional fractionation to provide product stream 54 and unreacted $C_3$'s 56. Byproduct isopropanol may be recovered as product stream 52 or converted in MTO or MTBE to produce additional hydrocarbons or ethers.

EXTRACTION UNIT OPERATION

Although the alcohol feedstock may comprise one or more $C_1$-$C_4$ lower aliphatic alkanols, the preferred crude material is methanol containing about 2 to 20%, preferably 4 to 17% by weight water. The extraction contact unit may be a stirred multi-stage vertical extraction column adapted for continuous operation at elevated pressure. Any suitable extraction equipment may be employed, including cocurrent, cross-current or single contactors, wherein the liquid methanol feedstock is intimately contacted with a substantially immiscible liquid hydrocarbon solvent, which may be a mixture of $C_4+$ aliphatic components including lower alkanes, n-alkenes or relatively pure isoalkenes, such as isobutylene, etc. This unit operation is described in Kirk-Othmer Encyclopedia of Chemical Technology (Third Ed.), 1980, pp.672-721. Other equipment for extraction is disclosed in DeFilipi et al U.S. Pat. No. 4,349,415, Tabak U.S. Pat. No. 4,626,415, and Arakawa et al U.S. Pat. No. 4,665,237. Unit operation details are also disclosed by Harandi et al in U.S. Pat. No. 4,777,321 and in copending U.S. patent application Ser. No. 179,726 (Docket 4751), filed Apr. 11, 1988, now U.S. Pat. No. 4,827,046 incorporated herein by reference. The methanol extraction step can be performed advantageously in a countercurrent multistage design, such as a simple packed column, rotating disk column, agitated column with baffles or mesh, or a series of single stage mixers and settlers.

TERTIARY ETHER PRODUCTION

The reaction of methanol with isobutylene and isoamylenes at moderate conditions with a resin catalyst is known technology, as provided by R. W. Reynolds, et al., *The Oil and Gas Journal,* June 16, 1975, and S. Pecci and T. Floris, *Hydrocarbon Processing,* December 1977. An article entitled "MTBE and TAME—A Good Otane Boosting Combo", by J. D. Chase, et al., *The Oil and Gas Journal,* Apr. 9, 1979, pages 149-152, discusses the technology. A preferred catalyst is a polysulfonic acid resin, such as "Amberlyst 15" resin. The acid etherification catalyst may also comprise medium pore metallosilicate. For instance, zeolite having the structure of zeolite beta or ZSM-5 may be employed.

Processes for producing and recovering MTBE and other methyl tert-alkyl ethers for $C_4$-$C_7$ isoolefins are known to those skilled in the art, such as disclosed in Osterburg et al U.S. Pat. No. 4,544,776 and Colaianne et al U.S. Pat. No. 4,603,225. Various suitable extraction and distillation techniques are known for recovering ether and hydrocarbon streams from etherification effluent.

MTO CONVERSION OF METHANOL TO HYDROCARBONS

Zeolite catalysis technology for upgrading lower aliphatic hydrocarbons and oxygenates to lower olefins and liquid hydrocarbon products are well known. Commercial Methanol-to-Gasoline (MTG), methanol-to olefins (MTO) and Mobil Olefin to Gasoline/Distillate (MOG/D) processes employ shape selective medium pore zeolite catalysts for these processes. It is understood that the present zeolite conversion unit operation can have the characteristics of these catalysts and processes to produce a variety of hydrocarbon products, especially $C_3$–$C_5$ olefins, and liquid aliphatic and aromatics in the $C_6$–$C_9$ gasoline range.

DESCRIPTION OF ZEOLITE CATALYSTS

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in Argauer, et al. U.S. Pat. No. 3,702,866, incorporated by reference.

Zeolite hydrocarbon upgrading catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity (alpha value) of about 1–250, preferably about 3 to 80 based on total catalyst weight. In the fluidized bed reactor the coked catalyst may have an apparent activity (alpha value) of about 3 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, and ZSM-48.

Aluminosilicate ZSM-5 is disclosed in U.S. Pat. No. 3,702,886 and U.S. Pat. No. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251, incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity.

Certain of the ZSM-5 type medium pore shape selective catalysts are sometimes known as pentasils. In addition to the preferred aluminosilicates, the gallosilicate, and ferrosilicate materials may be employed. ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt %, of the monoalkenes and methanol in a single pass. In the preferred embodiment 25% H-ZSM-5 catalyst calcined with 75% silica-alumina matrix binder is employed unless otherwise stated.

FLUIDIZED BED REACTOR OPERATION

Suitable feedstreams to the methanol conversion unit comprise various alcohols, such as methanol and, optionally, isopropanol obtained from the DIPE etherification operation. The reaction severity conditions can be controlled to optimize yield of the desired olefins, gasoline or $C_6$–$C_8$ BTX hydrocarbons, according to product demand by providing either fresh or regenerated catalyst having the desired properties. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

In a turbulent fluidized catalyst bed the conversion reactions are conducted in a vertical reactor column by passing hot reactant vapor upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion. In a typical process, the methanol and olefinic feedstream is converted in a catalytic reactor under moderate pressure (i.e.-100 to 2500 kPa).

Figure 2:
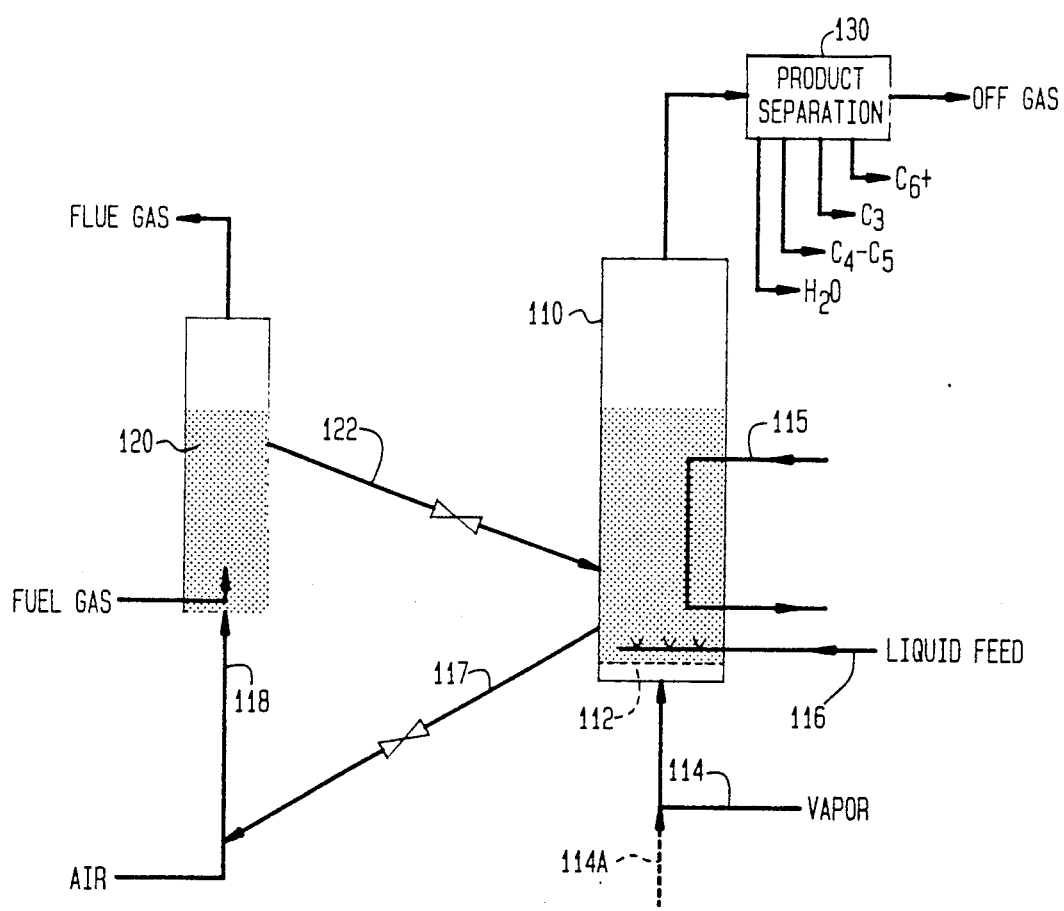

Referring now to FIG. 2, liquid methanol-containing raffinate 16 from the extractor is passed under pressure via feed conduit 116 for injection into vertical reactor vessel 110 above a feed distributor grid 112, which provides for distribution of hot vapor feed passing via conduit 114 through the small diameter holes in the grid 112. Fluidization is effected in the bottom portion of the bed by upwardly flowing gas introduced via conduit 114, which may be supplemented with additional reactive gas 114A, such as ethylenic fuel gas or the like. Thermodynamic conditions in the reaction vessel can be controlled by adjusting liquid injection rate, vapor feed temperature, catalyst temperature and rate, or by heat exchange means 115.

Provision is made for withdrawing catalyst from above grid 112 by conduit means 117 provided with flow control valve means to control passage via air lift line 118 to the catalyst regeneration system in vessel 120 where coked catalyst particles are oxidatively regenerated in contact with air or other regeneration gas at high temperature. Regenerated catalyst is returned to the reactor fluid bed 110 through conduit means 122 provided with flow control valve means. The hot regenerated catalyst is charged to the catalyst bed sufficiently below the upper interface to achieve good mixing in the fluid bed.

The product effluent separated from catalyst particles in the cyclone separating system then passes to effluent separation system 130. The product effluent is cooled and separated to recover a propene-rich $C_3$ stream, $C_4$–$C_5$ iso-olefins, $C_6$+ liquid gasoline range hydrocarbons, fuel gas, along with byproduct water. The preferred fluid bed reactor systems are described in Avidan et al U.S. Pat. Nos. 4,547,616; Harandi & Owen U.S. Pat. No. 4,751,338 ed; and in Tabak et al U.S. Pat. No. 4,579,999, incorporated herein by reference.

A typical single pass reactor unit employs a temperature controlled in the usual operating range of about 2500° C. to 650° C., preferably at average reactor temperature of 350° C. to 580° C., at moderate pressure of about 100 to 3000 kPa (atmospheric to about 400 psig). The weight hourly space velocity (WHSV, based on total alcohol in the feedstream) usually is about 0.1–5 WHSV.

DIPE REACTION

Olefin hydration to provide ethers and alcohols is well known. Reaction of propene with water to produce DIPE and byproduct isopropyl alcohol (IPA) is an acid catalyzed process step, as described in U.S. Pat. Nos. 4,214,107; 4,499,313 and pending application Ser. No. 139,571 filed Dec. 30, 1987 by Bell et al. The preferred catalytic methods for making DIPE employ solid acid catalysts, such as zeolites Y, Beta and/or ZSM-5 aluminosilicate. DIPE etherification conditions may vary widely in choice of temperature, pressure and reaction time. The preferred method of Bell et al reacts propene with water in a fixed bed of zeolite Beta at about 90° to 200° C. and pressure of at least 4000 kPa. However, it is understood that the unit operations described herein can be conducted with any number of specific process steps within the skill of the art.

The present invention is particularly advantageous in the economic dewatering of crude methanol, thus avoiding expensive and energy-intensive prefractionation by distillation. By extracting methanol from the crude feedstock with olefinic hydrocarbon reactant liquid, substantial utilities and equipment savings are realized. Various modifications can be made to the system, especially in the choice of equipment and non-critical processing steps.

To demonstrate the advantages of the invention, an integrated multi-reactor methanol conversion process according to the present invention is compared to a conventional prior art MTO single reactor process in Table 1, wherein the two continuous process flowrates are given in parts by weight, based on 100 parts methanol feedstock.

TABLE 1

Comparison of the Improved Process With MTO

|  | Crude Methanol | NET PRODUCT Prior MTO | Improved Process |
|---|---|---|---|
| $C_2^-$ |  | 4.9 | 4.7 |
| $C_3$'s |  | 11.4 | 5.2 |
| $C_4$'s |  | 9.6 | 4.5 |
| $C_5$'s |  | 5.3 | 3.4 |
| $C_6^+$ |  | 12.8 | 13.0 |
| Methanol | 100 |  |  |

TABLE 1-continued

Comparison of the Improved Process With MTO

|  | Crude Methanol | NET PRODUCT Prior MTO | Improved Process |
|---|---|---|---|
| MTBE |  |  | 7.5 |
| TAME |  |  | 2.5 |
| DIPE |  |  | 6.4 |
| $H_2O$ | 10 | 66 | 62.8 |
| Total | 110 | 110 | 110 |

The improved multi-reactor process makes 81% more $C_5+$ fuel from methanol than the conventional MTO process. In addition, the gasoline contains about 50% very high octane ethers. Table 2 gives material balances for the three reactors, based on 100 parts methanol feed.

TABLE 2

Reactors Material Balances for Converting Methanol to Ethers

|  | MTO RX FEED | MTO PRODUCT | MTBE/ TAME RX FEED | MTBE/ TAME RX EFFLUENT | DIPE RX FEED | DIPE RX EFFLUENT* |
|---|---|---|---|---|---|---|
| $C_2^-$ |  | 4.7 |  |  |  |  |
| $C_3$'s |  | 11.0 |  |  | 11.0 | 5.2 |
| $C_4$'s |  | 9.3 | 9.3 | 4.5 |  |  |
| $C_5$'s |  | 5.1 | 5.1 | 3.4 |  |  |
| $C_6^+$ |  | 12.4 |  |  |  | 0.6 |
| Methanol | 96.5 |  | 3.6 | 0.1 |  |  |
| MTBE |  |  |  | 7.5 |  |  |
| TAME |  |  |  | 2.5 |  |  |
| DIPE |  |  |  |  |  | 6.43 |
| $H_2O$ | 10.0 | 64 | 0.04 | 0.04 | 1.3 | 0.07 |
| Total | 106.5 | 106.5 | 18.04 | 18.04 | 12.3 | 12.3 |

*Assuming IPA is recycled to extinction.

While the invention has been described by specific examples, there is no intent to limit the inventive concept as set forth in the following claims.

We claim:

1. A continuous process for converting crude methanol to methyl tertiary-alkyl ether comprising the steps of:

(a) contacting a crude methanolic feedstock containing a minor amount of water with a liquid olefinic $C_4$–$C_5$ hydrocarbon extraction stream rich in $C_4$ or $C_5$ iso-alkene hydrocarbon or mixtures thereof under extraction conditions favorable to selective extraction of the methanol, thereby providing an extract liquid stream containing sufficient methanol for etherification and an aqueous raffinate stream lean in methanol;

(b) reacting liquid hydrocarbon extractant and extracted methanol substantially free of water in a first catalytic reaction zone in contact with acid etherification catalyst under etherification process conditions to convert methanol and iso-alkene hydrocarbon to predominantly methyl tertiary-alkyl ether;

(c) fractionating the etherification effluent from step (b) to recover liquid product containing methyl tertiary-alkyl ether;

(d) catalytically converting methanol in the raffinate stream at elevated temperature in contact with acid zeolite catalyst to produce predominantly lower olefins rich in propene, isobutylene and isoamylenes;

(e) reacting propene from methanol conversion step (d) with water to produce di-isopropyl ether; and (f) recovering the isobutylene and isoamylenes produced in step (d) by catalytic conversion of methanol in a $C_4$–$C_5$ liquid stream for recycle as liquid extractant.

2. The process of claim 1 wherein the acid etherification catalyst comprises sulfonic acid resin.

3. The process of claim 1 wherein the methanolic feedstock consists essentially of methanol and about 4 to 20 wt % water, and wherein the extraction liquid comprises at least 30l% by weight of $C_4$–$C_5$ tertiary-alkenes.

4. The process of claim 1 wherein the acid etherification catalyst comprises medium pore metallosilicate.

5. The process of claim 4 wherein the acid etherification catalyst comprises zeolite having the structure of zeolite beta or ZSM-5.

6. A process for converting crude aqueous alcohol feedstock to tertiary-butyl ether and tertiary-amyl ether product in contact with acid catalyst comprising the steps of:

contacting the aqueous alcohol feedstock with liquid hydrocarbon extractant comprising $C_4$–$C_5$ mixed olefinic hydrocarbons comprising isobutylene and isoamylenes under liquid extraction conditions;

recovering an aqueous raffinate phase containing a portion of feedstock alcohol and a major amount of water introduced with the feedstock;

recovering an organic extract phase comprising the hydrocarbon extractant and a major amount of alcohol introduced in the feedstock;

catalytically converting alcohol in the raffinate phase at elevated temperature in contact with acid zeolite catalyst to produce predominantly lower olefins rich in propene and isoalkene hydrocarbons; and reacting extracted alcohol with the isobutylene and isoamylenes under catalytic etherification reaction conditions to produce predominantly $C_5+$ t-alkyl ethers; and reacting propene from alcohol conversion with water in contact with olefin hydration catalyst to produce di-isopropyl ether.

7. The process of claim 6 wherein t-alkyl ether catalyst consists essentially of sulfonic acid resin and the crude feedstock contains methanol, ethanol or isopropanol and about 2 to 20 wt % water.

8. The process of claim 6 wherein said isoalkene produced by catalytic conversion of alcohol is recovered in a $C_4$–$C_5$ liquid stream and employed as liquid extractant.

9. The process of claim 6 wherein byproduct isopropanol is coproduced with di-isopropyl ether by reaction of propene with water; and wherein said isopropanol is converted to hydrocarbons concurrently with raffinate alcohol.

10. The process of claim 6 wherein byproduct isopropanol is coproduced with di-isopropyl ether by reaction of propene with water; and wherein at least a portion of said isopropanol is converted to t-alkyl ether by reaction with isobutylene or isoamylene.

11. The process of claim 6 wherein the liquid hydrocarbon extractant comprises $C_4$ mixed olefinic hydrocarbons comprising isobutylene, n-butenes, and butanes.

* * * * *